US00PP20640P2

(12) United States Plant Patent
Perkins

(10) Patent No.: US PP20,640 P2
(45) Date of Patent: Jan. 12, 2010

(54) ***ANGELONIA* PLANT NAMED 'CAR RASP'**

(50) Latin Name: *Angelonia angustifolia*
Varietal Denomination: Car Rasp

(75) Inventor: Ralph T. Perkins, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/291,432

(22) Filed: Nov. 10, 2008

(51) Int. Cl.
*A01H 5/00* (2006.01)

(52) U.S. Cl. ..... Plt./404

(58) Field of Classification Search ..... Plt./263, Plt./404

See application file for complete search history.

*Primary Examiner*—Susan B McCormick Ewoldt
(74) *Attorney, Agent, or Firm*—S. Matthew Edwards

(57) ABSTRACT

A new *Angelonia* plant named 'Car Rasp,' particularly distinguished by the red-purple flower color, upright and compact habit, with dense foliage, strong stems, and good floriferousness.

1 Drawing Sheet

Latin name of the genus and species of the plant claimed: *Angelonia angustifolia.*

Varietal denomination: 'Car Rasp'.

BACKGROUND OF THE NEW PLANT

The present invention comprises a new *Angelonia*, botanically known as *Angelonia angustifolia*, and hereinafter referred to by the variety name 'Car Rasp.'

'Car Rasp' is a product of a planned breeding program. The new cultivar 'Car Rasp' has a red-purple flower color, upright and compact habit, with dense foliage, strong stems, and good floriferousness.

'Car Rasp' originated from a hybridization in a controlled breeding program in Gilroy, Calif. USA. The female parent was an unpatented hybrid seedling identified as '347-1' with a blackberry color. '347-1' has a less upright habit, weaker branches, and less vigor than 'Car Rasp.'

The male parent of 'Car Rasp' was an unpatented hybrid seedling identified as '349-1' with a blackberry color. '349-1' is less floriferous, less branching and has darker foliage than 'Car Rasp.'

'Car Rasp' was selected as one flowering plant within the progeny of the stated cross in March 2006 in a controlled environment in Gilroy, Calif. USA. The pollination took place in August 2003 and the seed sowing in November 2005.

The first act of asexual reproduction of 'Car Rasp' was accomplished when vegetative cuttings were taken from the initial selection in March 2006 in a controlled environment in Gilroy, Calif. U.S.A.

Horticultural examination of plants grown from cuttings of the plant initiated in March 2006 in Gilroy, Calif. U.S.A, and continuing thereafter, has demonstrated that the combination of characteristics as herein disclosed for 'Car Rasp' are firmly fixed and are retained through successive generations of asexual reproduction.

'Car Rasp' has not been observed under all possible environmental conditions. The phenotype may vary significantly with variations in environment such as temperature, light intensity and day length.

Plant Breeder's Rights for this cultivar were applied for in Canada on Dec. 24, 2007 and in the European Union on Aug. 25, 2008. 'Car Rasp' has not been made publicly available more than one year prior to the filing of this application.

DESCRIPTION OF THE DRAWINGS

The accompanying photographic drawing shows typical flower and foliage characteristics of 'Car Rasp' with colors being as true as possible with an illustration of this type. The photographic drawing shows a flowering potted plant of the new variety and a close-up of the flowers. Both photographs were taken in Gilroy, Calif. U.S.A. in September 2007. The plants about 2–3 months old, grown in 4inch pots in a greenhouse.

DETAILED BOTANICAL DESCRIPTION

The measurements were taken in Gilroy, Calif. U.S.A., in April 2008 on plants that were growing in gallon pots in a greenhouse. Culture of these plants started about January 2008. These plants are about 3 months old.

Color Chart used: Royal Horticultural Society Colour Chart (R.H.S.) 2001

BRIEF SUMMARY OF INVENTION

The following observations, measurements, and comparisons describe plants grown outside in Gilroy, Calif. U.S.A. The following traits have been repeatedly observed and are determined to be basic characteristics of the new variety. The combination of these characteristics distinguishes this *Angelonia* as a new and distinct variety.

TABLE 1

DIFFERENCES BETWEEN THE NEW VARIETY 'CAR RASP' AND A SIMILAR VARIETY

| | 'Car Rasp' | 'Balangroki' |
|---|---|---|
| Flower color | Richer and deeper | Lighter, but not as rich |
| Flower size | Larger | Smaller |
| Plant habit | More upright | Less upright |

Plant:

*Form, growth and habit.*—Upright, compact, dense foliage, strong stems.

*Plant height.*—23–27 cm.
*Plant height* (*inflorescence included*).—28–32 cm.
*Plant width.*—18–21 cm.

Foliage:
*Immature, leaf color, upper surface.*—Closest to RHS 146A.
*Lower surface.*—RHS 146A.
*Mature, leaf color, upper surface.*—Closest to RHS 147A.
*Lower surface.*—RHS 146A.
*Length.*—5.2–6.1 cm.
*Width.*—1.6–1.8 cm.
*Shape.*—Elliptical.
*Base shape.*—Cunate.
*Apex shape.*—Acute.
*Margin.*—Slightly serrate.
*Texture.*—Hirsute; glandular hairs.
*Color of veins, upper and lower surfaces.*—RHS 144A.

Stem:
*Number of main stems per plant.*—4–5.
*Number of leaves per stem* (*before it branches*).—10–14.
*Color of stem.*—RHS 144B; anthocyanins of about RHS 166A in irregular patches.
*Length of stem.*—16–19 cm.
*Diameter.*—0.3–0.35 cm.
*Length of internodes.*—1.5–3.0 cm.
*Texture.*—Glandular hairs.

Inflorescence:
*Type.*—Terminal raceme; florets, solitary in leaf axis.
*Number of flowers per raceme.*—24–30.
*Raceme length.*—14–18 cm.
*Color of pedicel.*—RHS 144A mostly overlaid with anthocyanins of.
*Length of pedicel.*—0.9–1.0 cm.
*Diameter of pedicel.*—0.75 cm.
*Texture.*—Glandular hairs.

Corolla:
*Form.*—Single, two-lipped (5 petaled, fused at base).
*Length of floret.*—2.2–2.4 cm.
*Width of floret.*—2.1–2.3 cm.
*Color upper lip petals, upper surface.*—RHS 67A maturing to RHS N78C but with more grey and RHS 71D margins.
*Color upper lip petals, lower surface.*—RHS 77B but more grey.
*Size upper lip petal length.*—0.6 cm from corolla opening.
*Size upper lip petal width.*—0.9 cm.
*Color lower lip, lateral petals, upper surface.*—RHS 67A maturing to RHS N78C but with more grey and RHS 71D margins.
*Color lower lip, lateral petals, lower surface.*—RHS 77B but more grey.
*Size lower lip, lateral petals length.*—0.7–0.8 cm from corolla opening.
*Size lower lip, lateral petals width.*—0.7–0.8 cm.
*Color lower lip, mid-petal, upper surface.*—RHS 67A maturing to RHS N78C with RHS 71D margins, RHS 59B at throat, and slight spots of RHS N78A.
*Color lower lip, mid-petal, lower surface.*—RHS 77B but more grey.
*Size lower lip, mid-petal length.*—0.7–0.8 cm from corolla opening.
*Size lower lip, mid-petal width.*—0.7–0.8 cm.
*Petal shape.*—Obovate.
*Apex shape.*—Obtuse.
*Margin.*—Entire.
*Petal texture.*—Papillose and glandular hairs on both sides.
*Corolla color, inside.*—RHS 67A base color with RHS 59A hortizontal blotches.
*Corolla color, outside.*—RHS 77B base color with RHS 59A blotches.
*Duration of flowering.*—Continuous flowering throughout the Summer.
*Fragrance.*—None.
*Lastingness of individual florets.*—About 6–7 days.

Bud (just before opening):
*Color.*—RHS 58A.
*Length.*—0.6–0.8 cm.
*Width.*—0.4–0.5 cm.
*Shape.*—Obicular.
*Number of sepals.*—5 fused at base.
*Color of sepals.*—RHS 144A heavily overlaid with anthocyanins of closest to RHS N187A; RHS187A at the attachment to pedicel.
*Length of sepals.*—0.4–0.5 cm.
*Width of sepals.*—0.4 cm.
*Sepal shape.*—Ovate.
*Apex shape.*—Acute.
*Margins.*—Entire.
*Texture.*—Glandular hairs on both surfaces.

Reproductive organs:
*Pistil.*—1.
*Length.*—0.4 cm.
*Style color.*—RHS N155B.
*Stigma color.*—RHS 72D.
*Stamens.*—4, in pairs.
*Color of filaments.*—RHS N155B.
*Length of filaments.*—0.3 cm.
*Pollen amount.*—Very sparse.
*Color of pollen.*—Closest to RHS N92D.
*Fertility/seed set.*—Not observed on this hybrid.

Disease/pest resistance: Disease resistance or susceptibility has not been observed on this hybrid.

What is claimed is:

1. A new and distinct variety of *Angelonia* plant named 'Car Rasp,' substantially as illustrated and described herein.

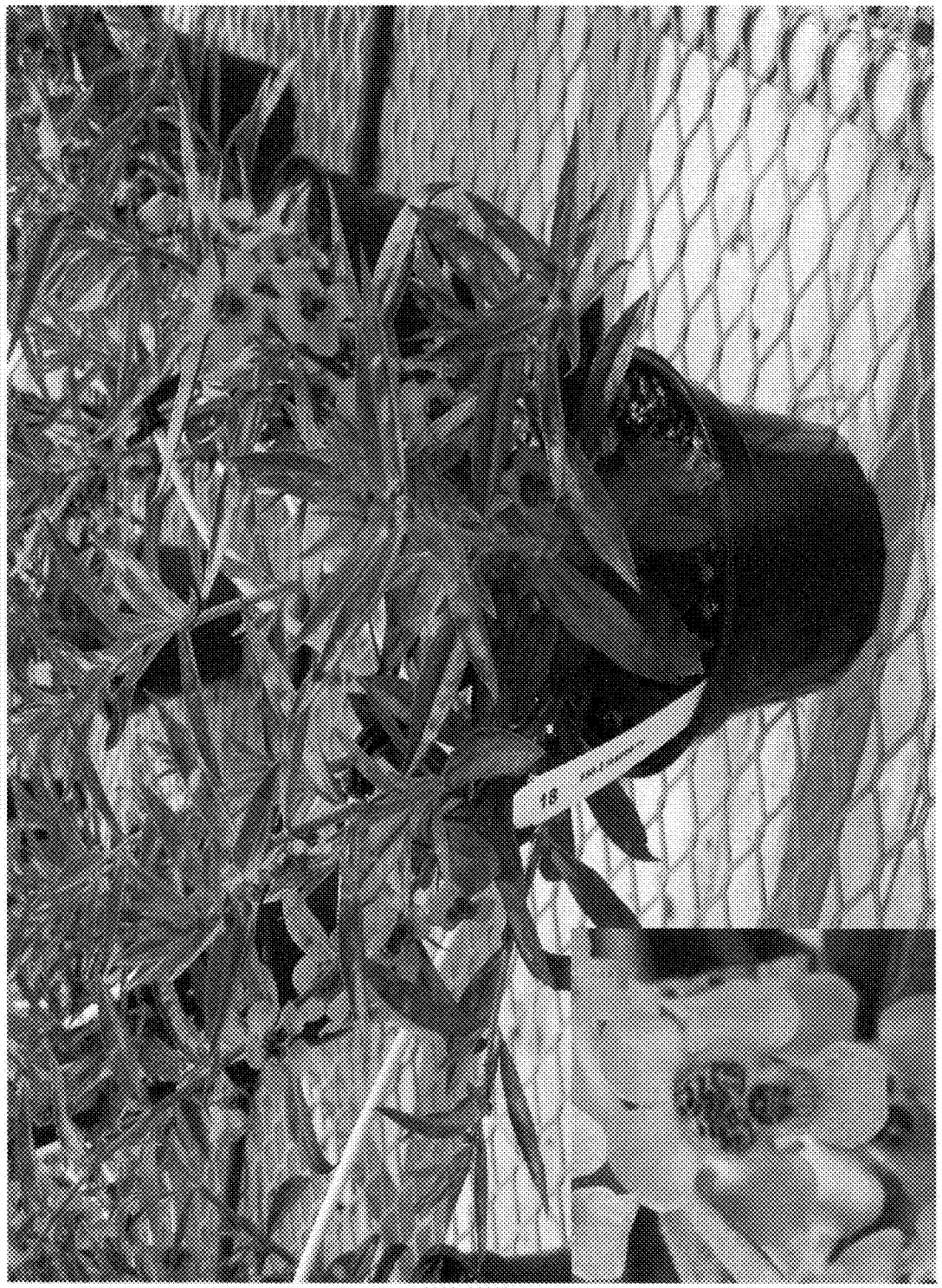

* * * * *